United States Patent [19]

Farzin-Nia et al.

[11] Patent Number: 5,429,501
[45] Date of Patent: Jul. 4, 1995

[54] ORTHODONTIC COIL SPRINGS AND METHODS

[75] Inventors: Farrokh Farzin-Nia, Inglewood, Calif.; Rohit C. L. Sachdeva, Plano, Tex.

[73] Assignee: Ormco Corporation, Glendora, Calif.

[21] Appl. No.: 219,031

[22] Filed: Mar. 28, 1994

[51] Int. Cl.⁶ .............................................. A61C 3/00
[52] U.S. Cl. .......................................... 433/21; 433/24
[58] Field of Search ................... 433/7, 20, 21, 24; 72/135, 371, 700

[56] References Cited

U.S. PATENT DOCUMENTS

| | | | |
|---|---|---|---|
| Re. 30,332 | 7/1980 | Wallshein | 433/20 |
| Re. 30,593 | 4/1981 | Wallshein | 433/20 |
| 3,593,421 | 7/1971 | Brader | |
| 3,988,832 | 11/1976 | Wallshein | |
| 4,197,643 | 4/1980 | Burstone et al. | 433/20 |
| 4,199,865 | 4/1980 | Cain | 433/21 |
| 4,256,456 | 3/1981 | Wallshein | 433/21 |
| 4,315,739 | 2/1982 | Cain | 433/21 |
| 4,849,032 | 7/1989 | Kawaguchi | 433/11.5 R |
| 5,046,948 | 9/1991 | Miura | 433/21 |
| 5,064,370 | 11/1991 | Jones | 433/21 |
| 5,074,784 | 12/1991 | Sterrett et al. | 433/21 |
| 5,120,218 | 6/1992 | Hanson | 433/19 |
| 5,137,446 | 8/1992 | Yamauchi et al. | 433/20 |
| 5,167,500 | 12/1992 | Miura | 433/7 |
| 5,199,869 | 4/1993 | McGann | 433/21 |
| 5,246,366 | 5/1993 | Tracey | 433/21 |
| 5,312,247 | 5/1994 | Sachdeva et al. | 433/7 |

Primary Examiner—Cary E. O'Connor
Attorney, Agent, or Firm—Wood, Herron & Evans

[57] ABSTRACT

Coil springs for use in orthodontic appliances which are made from wire of a beta-phase titanium alloy wound into a plurality of turns forming a coil having an outside diameter in the range of about 0.040 inches (1.016 mm) to about 0.075 inches (1.905 mm). These coil springs may be designed for use in tension as well as compression for a number of orthodontic applications.

35 Claims, 1 Drawing Sheet

ORTHODONTIC COIL SPRINGS AND METHODS

FIELD OF THE INVENTION

The present invention relates to orthodontic coil springs, and more particularly to such coil springs made from beta-phase titanium alloys.

BACKGROUND OF THE INVENTION

Springs are often used in orthodontic applications to supply a force for moving a patient's teeth. The force applied must be great enough for proper realignment of the tooth to occur. At the same time, however, when a patient's tooth is being moved, care must be taken not to apply too great a force to the tooth, otherwise resorption of the tooth root or some other harm to the tooth is likely to occur. Typically, posterior teeth require greater applied forces for movement than anterior teeth.

Springs of various shapes and sizes have been used throughout orthodontics, including finger springs, apron spring, coil springs, etc. In particular, coil springs made of stainless steel and nickel-titanium (Ni—Ti) alloys have been used in various orthodontic applications with a great deal of success even though these prior orthodontic coil springs have exhibited a number of disadvantages. Designing alternative coil springs with more optimum characteristics has proved very difficult.

Orthodontic coil springs made of stainless steel are relatively inexpensive and can be designed to provide sufficiently high applied forces to move a patient's teeth, even posterior teeth like molars. However, stainless steel coil springs are often unable to maintain a high enough applied force over a sufficient range of spring action (i.e., elastic change in spring length) without either some detrimental effect like tooth root resorption or the spring being too large to fit comfortably in the patient's mouth. In addition, because the force being applied by these springs typically diminishes very rapidly as the teeth start moving in the direction of force such springs have had to be replaced in order to obtain proper realignment of the teeth. Another disadvantage of stainless steel coil springs is that relatively low levels of deformation of the stainless steel material quickly results in permanent deformation of the spring. Stainless steels also contain elements, such as nickel, which have been known to cause adverse reactions in some patients.

Orthodontic coil springs have been successfully made of Ni—Ti alloys, but such springs are limited in their applications. Ni—Ti coil springs are typically able to maintain an applied load over broad ranges of spring action, but the forces applied by these springs are often too low to be useful in many orthodontic applications, in particular for distalizing posterior teeth such as molars. In addition, Ni—Ti alloys are relatively expensive and contain elements, such as nickel, which have been known to cause adverse reactions in some patients.

Therefore, there is a need in the orthodontic field for a more biocompatible coil spring design capable of exerting adequate applied forces over sufficient ranges of spring action to be useful in a greater number of orthodontic applications, including molar distalizing, without causing harm to the patient's teeth.

Reference has been made in the prior art, in particular U.S. Pat. No. 4,197,643, to the use of beta-phase titanium alloys for making orthodontic coil springs. Beta-phase titanium alloys are typically more expensive than stainless steel alloys and less expensive than Ni—Ti alloys. In addition, these alloys have well established biocompatibility. The '643 patent discloses a wide range of wire sizes, compositions and mechanical properties for use in making various types of orthodontic springs. The '643 patent, however, only suggests that coil springs made from such wire would be acceptable in orthodontic applications. Until the present invention, it was unknown which, if any, such beta-phase titanium alloy wires could be used successfully to make orthodontic coil springs. It was also previously unknown what, if any, coil spring designed with these wires would adequately perform in a broad enough range of orthodontic applications to supplant existing stainless steel and Ni—Ti coil springs.

SUMMARY OF THE INVENTION

The present invention is directed to coil springs for orthodontic applications which are able to exert a sufficiently high applied force to move a patient's tooth over a broad range of spring action, without causing harm to the tooth. The present invention is also directed to orthodontic appliances which incorporate the present coil springs.

The coil springs of the present invention are made with a wire of a beta-phase titanium alloy. Preferably, the crystal structure of the titanium alloy contains a minimum of about 90% of the beta-phase and the composition of the alloy contains a minimum of about 70% by weight titanium. The titanium base metal may be alloyed with molybdenum, chromium, zirconium, tin, vanadium, iron or columbium (i.e., niobium). Other alloying elements may also be suitable. Until now, it was unexpected that coil springs made from beta-phase titanium alloys would perform satisfactorily in any orthodontic application. Prior to the present invention, it was unknown whether such coil springs could apply enough force to move a tooth, including a molar, and yet not cause any detrimental effects, such as tooth root resorption. It was also unknown whether coil springs made from beta-phase titanium alloys could be designed to apply such a force over a sufficient range of spring action to cause proper realignment of the tooth, without the need for replacing the spring, while at the same time keeping the spring at a size which the patient's mouth could comfortably accommodate.

It has been discovered through extensive experimentation that such coil springs can be so designed using beta-phase titanium wire having a diameter in the range of about 0.008 inches (0.203 mm) to about 0.014 inches (0.355 mm), with the spring itself having an outside diameter in the range of about 0.040 inches (1.016 mm) to about 0.075 inches (1.905 mm), and an inside diameter in the range of about 0.020 inches (0.508 mm) to about 0.050 inches (1.270 mm). When used in some tension applications (i.e., initially in a closed coil condition and then extended to apply a force as it contracts), the present coil springs may have an active length in the range of about 5 mm (0.2 inches) to about 15 mm (0.59 inches). When used in some compression applications (i.e., initially in an open coil condition and then compressed to apply a force as it expands), the present coil springs may have an active length in the range of about 10 mm (0.39 inches) to about 30 mm (1.18 inches).

One feature of the present coil springs is their ability to apply a force in the range of about 100 grams to about 450 grams, or even higher, and maintain the applied force through an elastic change in spring length (i.e., range of spring action) of up to about 200%. Thus, the present coil springs may be used to move posterior as well as anterior teeth. In addition, full realignment of the tooth is more likely to be accomplished without having to replace the originally installed coil springs. Such mechanical properties may be attained by using beta-phase titanium alloy wires exhibiting a flexure modulus of elasticity within the range of about 4 million psi (2,812 Kg/mm$^2$) to about 15 million psi (10,545 Kg/mm$^2$).

The principles of the present invention, its objectives and advantages will be further understood with reference to the drawings and the following detailed description.

DETAILED DESCRIPTION OF THE INVENTION

Figure 1:
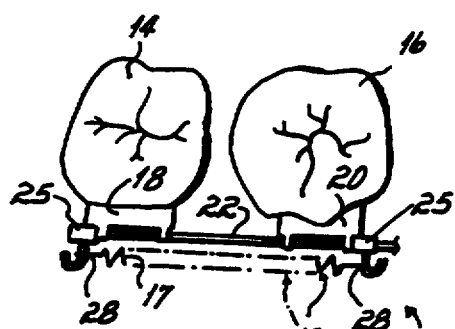
FIG. 1 is a partial plan view of an orthodontic appliance incorporating a tension coil spring according to the present invention mounted on a patient's teeth.
Figure 3:
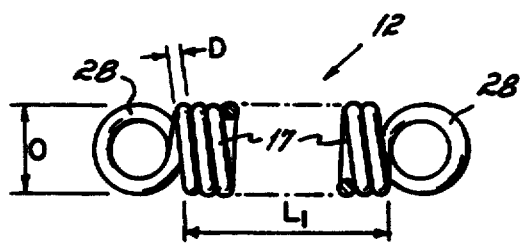
FIG. 3 is an enlarged side view of the tension coil spring of FIG. 1.
Figure 3A:
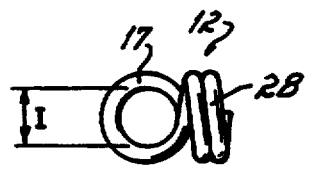
FIG. 3A is an enlarged end view of the tension coil spring of FIG. 3.

Referring to FIG. 1, for exemplary purposes only, a molar distalizing orthodontic appliance 10 is illustrated with a coil spring 12 incorporating principles of the present invention. The exemplary appliance 10, as illustrated, is being used to move molars 14 and 16 closer together. Therefore, coil spring 12 is of the tension type with a plurality of closed turns or loops 17 as illustrated in FIG. 3. The appliance 10 includes a pair of orthodontic brackets 18 and 20, each mounted respectively on molars 14 and 16. An arch wire 22 is connected to each bracket 18, 20. Each bracket 18, 20 mounts a stop fitting 25. The spring 12 includes an end hook or ring 28 at each of its ends. Each ring 28 is connected to a respective stop fitting 25. The initially closed coil tension spring 12 is stretched to connect the rings 28 to the stop fittings 25 in order for spring 12 to impart an applied force to move molars 14 and 16 toward one another, reducing the intervening space. The force used to initially stretch spring 12 when connecting rings 28 to stop fittings 25 is typically greater than the force applied by spring 12. Typically, it is more often necessary to move posterior teeth like molars apart rather than together. Thus, the present tension springs will likely see more use in moving anterior teeth together.

Figure 2:
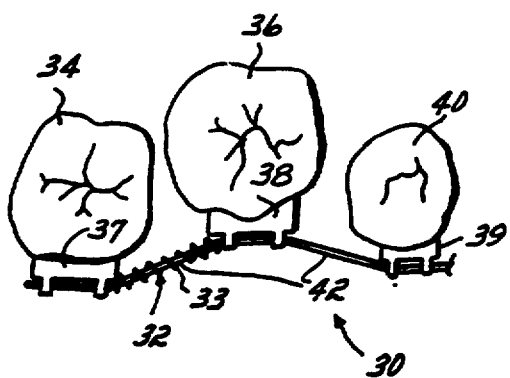
FIG. 2 is a partial plan view of an orthodontic appliance incorporating a compression coil spring according to the present invention mounted on a patient's teeth.
Figure 4:
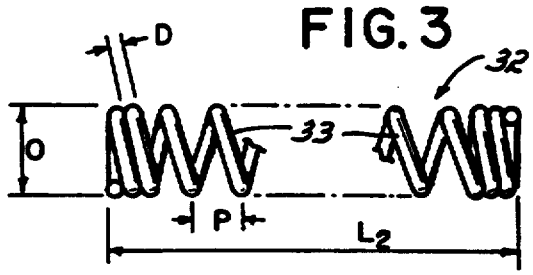
FIG. 4 is an enlarged side view of the compression coil spring of FIG. 2.
Figure 4A:
FIG. 4A is an enlarged end view of the compression coil spring of FIG. 4.

Referring to FIG. 2, in an alternative exemplary orthodontic appliance 30, a compression coil spring 32 with a plurality of open turns or loops 33, such as that shown in FIG. 4, is used to force two molars 34 and 36 apart. The appliance 30 includes two brackets 37 and 38, respectively fixed to molars 34 and 36 and a third bracket 39 fixed to bicuspid 40. An arch wire 42 is connected to each bracket 37, 38 and 39 in order to impart a force to straighten the teeth 34, 36 and 40. The compression spring 32 is disposed between the brackets 37 and 38 with its loops 33 disposed around the arch wire 42. Spring 32 is initially compressed when positioned between brackets 37 and 38 in order to impart an applied force to move teeth 34 and 36 away from each other, as spring 32 expands and molar 36 is pulled into alignment. Typically, the force used to initially compress spring 32 is greater than the force applied by spring 32 as it expands.

Referring to FIGS. 3 and 4, the present springs 12 and 32 are made with a wire of a beta-phase titanium alloy containing a minimum of about 70% by weight titanium. The crystal structure of the titanium alloy should also contain a minimum of about 90% of the titanium beta-phase. The titanium base metal may be alloyed with molybdenum, chromium, zirconium, tin, vanadium, iron or columbium (i.e., niobium). Satisfactory results have been obtained with both types of springs 12 and 32 by using an alloy for the wire containing, in weight percent, about 11.40% Mo, about 6.07% Zr, about 4.32% Sn and the balance being substantially Ti, with trace amounts of C (0.010%), Si (0.025%), Fe (0.030%), O (0.14%), Y (<0.001%), H (0.0130–0.0209%) and N (0.012%). Coil springs (tension and compression) according to the present invention have been successfully made with such beta-phase titanium alloy wires having diameters D of 0.008, 0.009 and 0.010 inches, with tolerances of ±0.0005 inches. However, it is believed that wire diameters D in the range of about 0.008 inches (0.203 mm) to about 0.014 inches (0.355 mm) could produce acceptable results. The typical mechanical properties of ultimate tensile strength (UTS), yield strength (YS), flexure modulus (E) and percent elongation (% El) for these three wires is compiled in Table I below.

TABLE I

| Wire Dia. (in.) | Typical Mechanical Properties | | | |
|---|---|---|---|---|
| | UTS (psi) | YS (psi) | E ($10^6$ psi) | % El (10″) |
| .008 | 184,600 | 103,000 | 4.75 | 3.52 |
| .009 | 178,400 | 101,000 | 4.27 | 4.48 |
| .010 | 181,600 | 130,000 | 6.37 | 4.39 |

The present coil springs 12 and 32 have an outside dimension or diameter O in the range of about 0.40 inches (1.016 mm) to about 0.075 inches (1.905 mm) and preferably in the range of about 0.050 inches (1.270 mm) to about 0.060 inches (1.524 mm). Coil springs 12 and 32 also have an inside dimension or diameter I in the range of about 0.020 inches (0.508 mm) to about 0.050 inches (1.270 mm), and preferably in the range of about 0.030 inches (0.762 mm) to about 0.040 inches (1.016 mm). The present tension springs 12 may be used in a variety of active lengths, such as active lengths $L_1$ in the range of about 5 mm (0.2 inches) to about 15 mm (0.59 inches) and more likely in the range of about 6 mm to about 13 mm. Acceptable results have been obtained with tension springs 12 made from the preceding 0.008, 0.009 and 0.010 inch diameter wires, each having an active length $L_1$ of approximately 10 mm (0.39 inches). Preferably, springs 12 have no gap between adjacent loops 17 and are kept as straight as possible.

Referring to FIG. 4, the present compression spring 32 may be used in a variety of active lengths, such as active lengths $L_2$ in the range of about 10 mm (0.39 inches) to about 30 mm (1.18 inches), and more likely in the range of about 15 mm to about 25 mm. Acceptable results have been obtained with compression springs 32 made from the preceding 0.008, 0.009 and 0.010 inch diameter wires, each having an active length $L_2$ of approximately 20 mm (0.79 inches). The compression spring 32 has an open coil pitch P in the range of about 0.010 inches (0.254 mm) to about 0.050 inches (1.270 mm), and preferably about 0.025 inches (0.635 mm). It is preferable for the present compression springs 32 to be as straight as possible.

The present coil springs are capable of applying forces in the range of about 100 grams to about 700 grams. Applied forces in the range of about 350 grams to about 450 grams have been found to be particularly useful in moving most, if not all, posterior teeth such as molars. However, in moving the posterior teeth (e.g., molar distalization) of some patients, it may be more efficient to use an applied force of up to about 700 grams. The mechanical properties of the alloy wire and, in turn, the present coil springs may be obtained by cold working the wire and then winding the wire into loops using a suitable mandrel to form the finished coil springs according to well known wire and coil spring forming techniques. The applied forces possible with the present coil springs may be maintained through an elastic change in active spring length $\Delta L$ (i.e., range of spring action) of up to about 200% displacement. The percent displacement is measured as the change in active length over the original active length.

Actual test data showing the relationship between the applied force in grams of load and the elastic change in active spring length $\Delta L$ in percent displacement for exemplary compression coil springs 32 is compiled in Table II below. The exemplary coil springs 32 tested were formed with the preceding 0.008, 0.009 and 0.010 inch diameter beta-phase titanium alloy (11.40%-Mo, 6.07%-Zr, 4.32%-Sn, and Bal.-Ti) wire having the mechanical properties in Table I. The outside diameter of each exemplary compression coil spring 32 was in the range of about 0.055 inches to about 0.060 inches.

TABLE II

| Percent Displacement | Applied Force vs. $\Delta L$ Load (g) | | |
|---|---|---|---|
| | .008" Wire | .009" Wire | .010" Wire |
| 0.0 | 0.0 | 0.0 | 0.0 |
| 7.7 | 30.0 | 44.0 | 51.0 |
| 15.4 | 60.0 | 93.0 | 112.0 |
| 23.2 | 87.5 | 137.0 | 172.0 |
| 30.8 | | 165.0 | 230.0 |
| 39.5 | 139.0 | 209.0 | 283.0 |
| 46.2 | | | 338.0 |
| 53.9 | 177.5 | 274.0 | 430.0 |
| 69.3 | 212.5 | 330.0 | |
| 75.3 | | 379.0 | |
| 84.6 | 279.0 | | |

The relationship between applied load and degree of displacement for these exemplary coil springs 32 was compared with that of similarly designed stainless steel (18% by wt.-Cr, 1% by wt.-Ni and, Bal.-Fe) and nickel-titanium alloy (50 at %-Ni and 50 at %-Ti) compression coil springs. The results of this comparison indicate that for similar coil spring configurations, in particular wire diameter and spring outside diameter, higher applied forces could be obtained for the same elastic change in active spring length using the present coil springs compared to the Ni—Ti coil springs. These results indicate that the present coil springs may not only be useful in replacing Ni—Ti coil springs in general orthodontic applications but particularly in molar distalizing and similar applications where relatively high applied forces are necessary. In comparing the exemplary coil springs 32 with similarly configured stainless steel coil springs, it appears that while such stainless steel coil springs can attain higher applied forces, they cannot maintain such forces over as great an elastic change in active spring length $\Delta L$ as the present coil springs. It is doubtful that the higher applied forces obtainable with such stainless steel coil springs would even be useful in a number of orthodontic applications because of the potential for such detrimental effects like tooth root resorption. Applied forces of up to about 700 grams to move teeth 34 and 36 apart may be applied using the compression spring 32 formed with about 0.0115 inch diameter beta-phase titanium alloy wire and having an outside diameter in the range of about 0.055 inches 0.060 inches. In some applications, even higher applied forces may be desirable. For example, a patient's teeth are sometimes moved in mass rather than individually. In such situations, while the plurality of teeth are being moved together, their positions relative to one another are maintained. Thus, any applied force is distributed among the teeth being moved, thereby requiring the coil spring to exert even higher applied force in order to move the teeth.

Thus, the present coil springs are able to apply enough force to move a patient's teeth, in particular the posterior teeth, without causing detrimental effects such as tooth root resorption. In addition, the broad range of possible applied force provides the present coil springs with the versatility to be useful in moving smaller anterior teeth (bicuspids, canines and incisors) as well as larger posterior teeth (molars). Because the applied forces exerted by the present coil springs can be maintained over broad ranges of spring action, full realignment of the patient's teeth is more likely to be accomplished without having to replace the coil springs. At the same time, the present coil springs may be kept at a size which a patient's mouth can comfortably accommodate.

While the idea of using beta-phase titanium alloys to make orthodontic coil springs was previously disclosed in U.S. Pat. No. 4,197,643, which is incorporated herein by reference in its entirety, until now, it was unexpected that coil springs made from beta-phase titanium alloys would in fact perform satisfactorily in orthodontic applications. The '643 patent only suggests that a wire of a beta-phase titanium alloy can be used to make coil springs suitable for orthodontic applications. The '643 patent does not contain any specific disclosures, like actual examples, indicating that such coil springs would actually be suitable for use in any orthodontic applications, let alone for molar distalizing.

From the above disclosure of the general principles of the present invention and the preceding detailed description, those skilled in the art will readily comprehend the various modifications to which the present invention is susceptible. For example, while the present invention has been described with regard to a coil spring having circular loops, it is understood that the principles of the present invention may be equally applicable to coil springs having a variety of loop configurations (e.g., square, rectangular, oval, etc.). Therefore, the scope of the present invention should be limited only by the following claims and equivalents thereof.

What is claimed is:

1. An orthodontic appliance comprising:

an element mountable to a tooth; and a coil spring connected to said element for applying a force to move the tooth when said element is mounted thereto, said coil spring having an outside diameter in the range of about 0.040 inches (1.016 mm) to about 0.075 inches (1.905 mm) and being made with a wire of a beta-phase titanium alloy.

2. The appliance of claim 1, said coil spring having an inside diameter in the range of about 0.020 inches (0.508 mm) to about 0.050 inches (1.270 mm).

3. The appliance of claim 1, said wire having a diameter in the range of about 0.008 inches (0.203 mm) to about 0.014 inches (0.355 mm).

4. The appliance of claim 1, said coil spring being an tension spring having an active length in the range of about 5 mm to about 15 mm.

5. The appliance of claim 1, said coil spring being a compression spring having an active length in the range of about 10 mm to about 30 mm.

6. The appliance of claim 5, said beta-phase titanium alloy containing at least one alloying element from the group consisting of molybdenum, chromium, zirconium, tin, vanadium, iron, and columbium.

7. The appliance of claim 1, said beta-phase titanium alloy containing a minimum of about 70% by weight titanium.

8. The appliance of claim 1, said titanium alloy having a crystal structure containing a minimum of about 90% beta-phase.

9. The appliance of claim 1, said coil spring being able to apply a force in the range of about 100 grams to about 450 grams.

10. The appliance of claim 1, said coil spring being able to apply a force in the range of about 350 grams to about 450 grams.

11. The appliance of claim 1, said coil spring being able to apply a force of up to about 700 grams.

12. The appliance of claim 1, said coil spring being able to maintain an applied force through an elastic change in spring length of up to about 200%.

13. An orthodontic coil spring comprising:

a wire of a beta-phase titanium alloy wound into a plurality of turns forming a coil having an outside diameter in the range of about 0.040 inches (1.016 mm) to about 0.075 inches (1.905 mm).

14. The coil spring of claim 13 having an inside diameter in the range of about 0.020 inches (0.508 mm) to about 0.050 inches (1.270 mm).

15. The coil spring of claim 13, said wire having a diameter in the range of about 0.008 inches (0.203 mm) to about 0.014 inches (0.355 mm).

16. The coil spring of claim 13 being a tension spring having an active length in the range of about 5 mm to about 15 mm.

17. The coil spring of claim 13 being a compression spring having an active length in the range of about 10 mm to about 30 mm.

18. The coil spring of claim 13, said beta-phase titanium alloy containing a minimum of about 70% by weight titanium.

19. The coil spring of claim 18, said beta-phase titanium alloy containing at least one alloying element from the group consisting of molybdenum, chromium, zirconium, tin, vanadium, iron, and columbium.

20. The coil spring of claim 13, said titanium alloy having a crystal structure containing a minimum of about 90% beta-phase.

21. The coil spring of claim 13 being able to apply a force in the range of about 100 grams to about 450 grams.

22. The coil spring of claim 13 being able to apply a force in the range of about 350 grams to about 450 grams.

23. The coil spring of claim 13 being able to apply a force of up to about 700 grams.

24. The coil spring of claim 13 being able to maintain an applied force through an elastic change in spring length of up to about 200%.

25. An orthodontic coil spring comprising:

a wire of a titanium alloy having a crystal structure containing a minimum of about 90% beta-phase and a composition containing a minimum of about 70% by weight titanium, said wire having a diameter in the range of about 0.008 inches (0.203 mm) to about 0.014 inches (0.355 mm) and being wound into a plurality of turns forming a coil having an outside diameter in the range of about 0.040 inches (1.016 mm) to about 0.075 inches (1.905 mm).

26. The coil spring of claim 25 being able to apply a force in the range of about 100 grams to about 700 grams and maintain said force through an elastic change in spring length of up to about 200%.

27. A method of moving a tooth comprising the steps of:

providing an orthodontic appliance comprising:
an element mountable to a tooth, and
a coil spring having an outside diameter in the range of about 0.040 inches (1.016 mm) to about 0.075 inches (1.905 mm) and being made with a wire of beta-phase titanium alloy;

mounting the element to the tooth; and applying a force to move the tooth by connecting the coil spring to the element.

28. The method of claim 27 including the steps of:

providing the orthodontic appliance with a compression coil spring, and applying the force to move the tooth away from another tooth by connecting the compression coil spring to the element.

29. The method of claim 27 including the steps of:

providing the orthodontic appliance with a tension coil spring, and applying the force to move the tooth toward another tooth by connecting the tension coil spring to the element.

30. The method of claim 27 including the step of:

applying a force in the range of about 100 grams to about 450 grams to move the tooth by connecting the coil spring to the element.

31. The method of claim 27 including the step of:

applying a force in the range of about 350 grams to about 450 grams to move the tooth by connecting the coil spring to the element.

32. The method of claim 27 including the step of:

applying a force of up to about 700 grams to move the tooth by connecting the coil spring to the element.

33. A method of making a coil spring suitable for orthodontic applications comprising the steps of:

providing a wire of a beta-phase titanium alloy;

winding the wire into a plurality of turns, thereby forming a coil having an outside diameter in the range of about 0.040 inches (1.016 mm) to about 0.075 inches (1.905 mm).

34. The method of claim 33 including the steps of winding the wire into a plurality of open turns, thereby forming an open coil, and
cutting the open coil into a plurality of lengths, and forming each length of open coil into a compression spring having an active length in the range of about 10 mm to about 30 mm.

35. The method of claim 33 including the steps of:
winding the wire into a plurality of substantially closed turns, thereby forming a closed coil,
cutting the closed coil into a plurality of lengths, and forming each length of the closed coil into a tension spring having an active length in the range of about 5 mm to about 15 mm.

* * * * *